United States Patent [19]

Rosén

[11] Patent Number: 5,439,802
[45] Date of Patent: Aug. 8, 1995

[54] METHOD FOR DETERMINING THE FUNCTIONAL ACTIVITY OF FREE PROTEIN S OR PROTEIN C IN A PLASMA SAMPLE

[75] Inventor: Steffen Rosén, Kallered, Sweden

[73] Assignee: Chromogenix AB, Molndal, Sweden

[21] Appl. No.: 793,342

[22] PCT Filed: Jul. 4, 1990

[86] PCT No.: PCT/SE90/00478
§ 371 Date: Jan. 14, 1992
§ 102(e) Date: Jan. 14, 1992

[87] PCT Pub. No.: WO91/01382
PCT Pub. Date: Feb. 7, 1991

[30] Foreign Application Priority Data

Jul. 14, 1989 [SE] Sweden .................. 8902532

[51] Int. Cl.$^6$ .................. C12Q 1/56; G01N 33/86; G01N 33/00; A61K 37/00
[52] U.S. Cl. .................. 435/13; 435/4; 435/226; 436/69; 436/86; 514/21; 530/393
[58] Field of Search .................. 435/13, 226, 4; 436/86, 436/69; 514/21; 530/393

[56] References Cited

U.S. PATENT DOCUMENTS

| | | | |
|---|---|---|---|
| 4,657,894 | 4/1987 | Zimmerman et al. | 514/21 |
| 4,775,624 | 10/1988 | Bang et al. | 435/226 |
| 4,908,314 | 3/1990 | Orthner | 435/13 |
| 5,001,069 | 3/1991 | Bartl et al. | 436/86 |
| 5,051,357 | 9/1991 | Hassouna | 436/69 |
| 5,059,525 | 10/1991 | Bartl et al. | 436/69 |
| 5,084,273 | 1/1992 | Hirahara | 530/393 |

OTHER PUBLICATIONS

Stedmos Medical Dictionary, 24 Edition, (1982), p. 1448.
Bartl et al (Abstract); Chem. Abstract; 89(1):2596K (1978).

*Primary Examiner*—Michael G. Wityshyn
*Assistant Examiner*—Louise N. Leary
*Attorney, Agent, or Firm*—Birch, Stewart, Kilasch & Birch

[57] ABSTRACT

The present invention involves the determination of Protein S and Protein C activity in human plasma based on the addition of FIX$_a$ which indirectly influences the formation of thrombin.

16 Claims, 3 Drawing Sheets

METHOD FOR DETERMINING THE FUNCTIONAL ACTIVITY OF FREE PROTEIN S OR PROTEIN C IN A PLASMA SAMPLE

The present invention relates to the assay of components in the blood coagulation and fibrinolysis systems, and particularly to the assaying or determination of the functional activity of certain proteins included in these systems, namely the plasma proteins designated Protein C and Protein S.

One purpose of the blood coagulation or clotting process is to effectively stop bleeding. This process involves a complicated so-called enzymatic cascade of enzyme-activating reactions initiated by contact activation, e.g. through an injured blood vessel, of a proenzyme, Factor XII (the word Factor is abbreviated hereinafter to F, as is normal practice) to an active enzyme $FXII_a$ (the suffix "a" stands for active and this labelling method is used generally in the following text). $FXII_a$ catalyzes a subsequent activation reaction of proenzyme to enzyme and the blood coagulum or blood clot is finally formed through a series (cascade) of enzyme activations, by the conversion of soluble fibrinogen to insoluble fibrin. The many activation stages, i.e. the cascade of reactions, contribute to the rapid formation of the blood clot, so as to stop bleeding rapidly.

The reverse process, i.e. the lysis of formed blood clots, so-called fibrinolysis also comprises a similar enzyme reaction cascade, wherein plasmin is formed, in the ultimate stage of the cascade. The plasmin formed functions to degrade the clot, i.e. the fibrin, quickly into smaller, soluble fragments, by proteolysis.

These systems incorporate a large number of factors, as will be described in more detail herebelow.

Enhanced or reduced quantities of one or more of these factors in the blood, due to acquired or inherited disorders in the coagulation and/or fibrinolysis systems will often lead to pathological conditions, which may be fatal, and in the case of the individual may, for instance, mean a predisposition to the formation of arterial and/or venous thrombosis (or blood clots). Reduced quantities of functionally active antithrombin and plasminogen and enhanced quantities of FVII, fibrinogen and plasminogen activator inhibitors PAI-1 are examples of disorders which can lead to thrombosis (or blood clots).

Recently, two novel proteins, designated Protein C (PC) and Protein S (PS) have been identified in plasma. Similar to the well-known antithrombin, these proteins, which are vitamin K dependent, have an anticoagulating activity, said proteins coacting such that Protein S (molecular weight 80 kD) will stimulate the activity of activated Protein C and therewith both counteract clot formation and promote degradation of clots that have already formed. Reduced quantities of these proteins, or of one of said proteins, will also lead to disorders in the coagulation and fibrinolysis systems. The significance of Protein S has been confirmed by studies carried out on the protein. On the basis of these studes, it is believed that in the case of patients afflicted with deep venous thrombosis and younger than 50 years of age, the clinically manifested thrombosis in 5–8% of cases is due to an inherited deficiency of Protein S, whereas an inherited deficiency of antithrombin is believed to be responsible for only about 3% of all cases.

Considerable benefit would therefore be gained if it were possible to assay, or. determine the content of, both or one of the proteins as a matter of routine, since this will enable the predisposition of an individual to the formation of such thrombosis to be established more easily and to enable prophylaxis and/or therapeutic treatment to be administered in good time.

These plasma proteins, PC and PS, influence the formation of $FX_a$ and thrombin, by coacting to cleave the cofactors $FV_a$ and $FVIII_a$, necessary for effecting formation of thrombin. In order to facilitate an understanding of the function of Protein S and Protein C (in an activated form), a brief description is given below of the essential parts of the coagulation system, of which the stages from and including activation of FXII are shown in Schedule 1:

Schedule 1

-continued

As will be seen from this schedule (1), the inactive protein prothrombin (proenzyme) is converted to active thrombin (enzyme), through the influence of activated FX, i.e. $FX_a$, $Ca^{2+}$, a phospholipid designated TF3 (thrombocyte factor 3) which is exposed on the surface of activated thrombocytes, and a helper-protein FV in its activated form $FV_a$. The thrombin cleaves the fibrinogen enzymatically, such as to obtain fibrin, which forms the structural framework of the clot, by being cross-linked with the aid of the enzyme $FXIII_a$. These processes are illustrated in Schedule 2 below, which thus forms part of Schedule 1.

In turn, $FX_a$ has been formed by inactive FX through the action of $FIX_a$ and with the aid of TF3, $Ca^{2+}$ and a further helper protein FVIII in the active form $FVIII_a$. These processes are illustrated in Schedule 3 below, which also forms part of Schedule 1.

As will be seen from these schedules, thrombin is self-regulating with respect to the quantity formed, by contributing to the activation of $FV_a$ (Schedule 2) and, together with $FX_a$, also to the activation of $FVIII_a$ (Schedule 3), these active factors being necessary for effective thrombin formation, and also by contributing to the activation of Protein C which, in active form, together with Protein S decreases thrombin formation by cleaving the factors $FVIII_a$ and $FV_a$, as will be explained here below.

The enzyme $FIX_a$ is formed by inactive FIX through the action of $FXI_a$ and $Ca^{2+}$. $FXI_a$ has been obtained by FXI through the action of $FXII_a$. $FXII_a$ is formed by FXII as a result of vessel injury or the like, which consequently is the initiating factor in the clotting system. This is illustrated in Schedule 4 below, which also forms part of Schedule 1.

Schedule 4

In addition to the processes disclosed in Schedule 2 and Schedules 3+4, the formation of thrombin is promoted by activation of FIX and FX to $FIX_a$ and $FX_a$ respectively, via the extrinsic system with the assistance of a tissue factor, tissue thromboplastin, which supplies helper-protein and phospholipid, and by the action of the enzyme $FVII_a$ in the presence of $Ca^{2+}$.

The activated forms of the coagulation and fibrinolysis factors do not normally occur in the blood, but are only formed when needed. The blood contains a number of proteins, so-called enzyme inhibitors, which guard against erroneous activation. One well known inhibitor is antithrombin, which binds thrombin to a complex lacking proteolytic activity.

Protein C (PC) and Protein S (PS), to which the present invention relates, also act as inhibitors or anticoagulants, the effect of these proteins being based on the activation of Protein C to active Protein C, APC, which cleaves $FV_a$ with the assistance of Protein S. This reduces the conversion of pothrombin to thrombin (Schedule 5) dramatically, and thus the formation of clots.

Schedule 5

In addition, APC exerts, together with PS, a cleaving effect on $FVIII_a$, which also assists in the anticoagulating effect, by reduced formation of $FX_a$. This process is illustrated in Schedule 6 below.

Schedule 6

As will be seen from these schedules, the activation of Protein C is controlled by some kind of feedback mechanism which incorporates thrombin for the purpose of restricting clot formation. When clots are formed in a blood vessel, thrombin is passed from the clot to the vessel wall, where thrombin is bound to thrombomodulin (TM), which is a protein on the endothelial cell surface. After becoming bound, thrombin no longer has a coagulating effect, i.e. it is no longer able to cleave the fibrinogen, and instead the complex TM/thrombin quickly activates Protein C to APC which, in the form of a complex with Protein S, inhibits coagulation by cleaving $FV_a$ and $FVIII_a$. This latter complex thus has an important anti-clotting effect.

As mentioned earlier, APC also promotes clot lysis. This takes place indirectly, by protection of the tissue plasminogen activator (t-PA) against the effect of inhibitors. In this way, a high conversion rate of plasminogen to plasmin is maintained, through the effect of t-PA. Plasmin dissolves the fibrin clot, by cleaving the clot into smaller, soluble fragments.

Too low contents of Protein C and/or Protein S, will render an individual predisposed to thrombotic diseases, as a result of insufficient moderation of thrombin formation, which results in excessive formation of fibrin with the accompanying risk of thrombosis. Consequently, there is a need of a simple and safe process by means of which the levels of Protein C and/or Protein S in a sample can be measured in a routine fashion, so as to enable prophylaxis and/or therapeutic treatment of thrombosis to be improved. It is the functional activity of Protein C and/or Protein S which shall be determined in particular, since about 10% of all individuals suffering from a Protein C deficiency exhibit normal immunological levels of Protein C, despite the fact that the functional activity is greatly reduced or totally lacking. With regard to Protein S, the concentration of which in plasma is about 22 μg/ml, the greater part thereof, about 60%, is bound to a protein within the complementary system, the C4b-binding protein, and is functionally inactive. The remainder, about 10 μg/ml, which is present in a free state in plasma, is responsible for the biological activity, i.e. is bound to activated Protein C to form an active complex. Since individuals suffering from a Protein S deficiency can exhibit normal levels of bound Protein S, despite lacking or exhibiting very low levels of free Protein S, it is the functional activity which shall be measured also in the case of Protein S deficiency.

Hitherto, however, no satisfactory process has been developed for assaying the functional activity of primarily Protein S.

The functional activity of Protein S has, admittedly, been the subject of earlier assaying methods, although not as matter of routine, and the known methods are not sufficiently reliable with respect to distinguishing between various levels of biological activity. Those methods known at present are based on recording the time at which a fibrin clot occurs. These methods are designated APTT-based or $FX_a$-based coagulation methods, the abbreviation "APTT" standing for "Activated Partial Thromboplastin Time". In this regard, plasma is activated in a first stage with a reagent containing phospholipid and a contact activator, such as kaolin or ellaginic acid, thereby initiating the calcium-dependent coagulation reactions (see Schedule 4), i.e. $FXII_a$ and $FX_a$. $Ca^{++}$-ions are added in a second stage, wherewith FIX, FX and prothrombin are activated to varying degrees. A known quantity of one or more coagulation factors is also added, for the purpose of determining the Protein S activity.

The coagulation sequence initiated in stage 1 thus proceeds to completion, so as to form a blood clot. The time (in seconds) taken for the clot to form (APTT) is recorded and correlated to the functional activity of Protein S, with the aid of standard samples. Generally, an increasing content of free Protein S in plasma will require a longer time for a blood clot to form, since larger quantities of the coagulation inhibiting APC/-Protein S-complex are formed.

The activating coagulation factors added to the system in these known methods are activated Protein C (APC) and $FX_a$ [see P. COMP and C. ESMON, "Recurrent Venous Thromboembolism in Patients with a Partial Deficiency of Protein S", New Eng. J. Med. 311, 1525–1528 (1984), and B. DAHLBÄCK, "Inhibition of Protein $C_a$ Cofactor Function of Human and Bovine Protein S by C4b-Binding Protein", (1986)]. According to A. d'ANGELO, S. VIGANO-d'ANGELO, C. ESMON, P. COMP, "Acquired Deficiencies of Protein S. Protein S Activity During Oral Anticoagulation, in Liver Disease and in Disseminated Intravascular Coagulation". J. Clin Invest 81, 1445–1454 (1988), first free Protein S in plasma is extracted with the aid of a specific monoclonal antibody, whereafter APC and $FX_a$ are added to the extracted protein. In K. SUZUKI and J. NISHIOKA, "Plasma Protein S Activity Measured Using Protac, a Snake Venom Derived Activator of Protein C", Thromb Res. 49, 241–251 (1988), there is used, instead of APC, a substance which activates PC in plasma to APC, namely Protac ® C (from Pentapharm, Switzerland), the active component of which is a selective snake venom enzyme from Agkistrodon Contortfix contortrix.

These known methods, however, have several drawbacks. For instance, the low resolution, i.e. the discrimination of different levels of free Protein S, is limited. Typically, the coagulation time is extended by only 10 s within the range of 70–200% free Protein S, the coagulation time for normal plasma, i.e. 100% free Protein S, lying within a range of 40–80 s, depending on the method used. Furthermore, these methods are difficult to carry out on a routine basis, e.g. in coagulation laboratories, and require thorough standardization and are deficient with respect to accuracy.

Accordingly, it is an object of the present invention to provide a method for assaying the levels of functionally active Protein S or Protein C in blood plasma, which can be carried out simply and which will essentially circumvent the drawbacks associated with known methods.

In accordance with the invention, this object is achieved with a method comprising the addition of the coagulation enzyme $FIX_a$, this enzyme promoting the formation of the coagulation enzyme $FX_a$, optionally together with further coagulation reagent(s), to a plasma sample whose content of functionally active Protein S or Protein C shall be determined, incubating the sample and measuring, in a known manner, the amount of thrombin derived from prothrombin, this process being catalyzed by $FX_a$, and measuring the content of functionally active Protein S or Protein C, which is inversely correlated to the amount of thrombin formed, on the basis of the measured quantity of thrombin in a known manner with the aid of a standard.

Thus, the quantity of thrombin formed constitutes a measure of the quantity of functionally active Protein S or Protein C present. Methods for assaying the thrombin content in plasma are well known, and the invention is not limited to any particular measuring method. All methods known at present and also those methods which may be devised in the future are usable. Examples of suitable measuring methods include substrate cleaving based, preferably photometric, measuring processes and coagulation-based measuring processes.

In accordance with the invention, it is found that the photometric substrate-cleaving method is well-suited for determining the functional activity of Protein S and Protein C on the basis of the quantity of thrombin formed, and this method provides considerably greater resolution than that achieved with the known coagulation-based methods, particularly with respect to Protein S. According to one preferred embodiment of the invention, photometric measurement of the quantity of thrombin formed is therefore applied, wherein a selective thrombin substrate, preferably a chromogenic thrombin substrate, is used. Such substrates are normally based on amino acids or, preferably, on short peptides which are provided with a group (marker) which can be readily and selectively cleaved by thrombin and can be readily measured, e.g. photometrically, when a chromogenic marker, such as p-NA (p-nitroaniline) is used. These substrates are available commercially, for instance, from Kabi Diagnostica, Mölndal, Sweden and/or can be easily prepared by the person skilled in this art.

It is also surprisingly found, in accordance with the invention, that by suitable selection of the selective thrombin substrate, the inventive method can be carried out optionally in either two stages or in one single stage. It is thus surprising and beneficial that the method can be carried out in one single stage when a suitable selective substrate is chosen. The substrates which make a single-stage process possible are, for instance, H-D-Ala-Pro-Arg-pNA (S-2846) (from KabiVitrum AB, Sweden) and H-D-CHG-Ala-Arg-pNA (Nycomed Th-1) (from Nycome AS, Norway). The known thrombin substrate H-D-Phe-Pip-Arg-pNA (S-2238) (from KabiVitrum AB, Sweden), on the other hand, is not suited for a single-step process, due to insufficient resolution among other things.

The inventive method also enables the quantity of thrombin formed to be established with the aid of coagulation methods in a known manner. The coagulation sequence is therewith permitted to proceed to completion and the time taken for a clot to form on the plasma sample is measured and compared with corresponding times for plasma with known functional activity of Protein S or Protein C. The process can be carried out in either one stage or in two stages.

The present method is based on an addition of $FIX_a$ for promoting activation of FX to $FX_a$, instead of adding $FX_a$ directly, as is often the case when practicing prior art methods. The $FIX_a$ used in accordance with the invention is normally of mammal origin, e.g. from bovine. $FIX_a$ from humans or pigs can also be used with advantage.

Addition of $FIX_a$ in accordance with the invention provides the advantage of enabling activation of FX to $FX_a$ to be controlled and, indirectly, also of enabling the inactivating effect of APC/PS on formed $FV_a$ and $FVIII_a$ to be optimized, which in turn greatly influences the formation of thrombin. The strong influence of $FIX_a$ on the process, for instance in comparison with the addition of $FX_a$ at corresponding plasma contents, could not be foreseen. Neither has the addition of $FIX_a$ for the purpose intended with the invention been earlier described.

The inventive method can be further improved by adding certain other coagulation factors, in addition to $FIX_a$. Thus, according to one preferred embodiment, the method is carried out while adding activated Protein C, i.e. APC. The APC used is normally of mammal origin, such as from bovine (bovine APC) or pig (porcine APC) or preferably from humans (human APC). Usable APC can be prepared from plasma or by recombinant techniques, and is normally highly purified. The earlier mentioned commercial preparation Protac ® C including a snake venom enzyme can be used instead of APC. This enzyme activates Protein C to APC and thus promotes indirectly formation of the APC/PS complex, the effect of which has been discussed earlier.

According to a further suitable embodiment of the invention, $FV_a$ is also added to the plasma sample. The addition of $FV_a$ is used to control the rate at which thrombin is formed, and the conversion of prothrombin to thrombin can be effected more quickly and more efficiently by the suitable addition of $FV_a$. There is preferably used an $FV_a$ of mammal origin, such as human origin, bovine origin or porcine origin, and preferably bovine origin, $FV_a$ prepared from plasma or via recombinant techniques.

Phospholipid is another coagulation reagent which can be appropriately added to the plasma sample when carrying out the present invention. This addition is able to accelerate the activation of FX to $FX_a$ and prothrombin to thrombin. The choice of the phospholipid source is not critical. For instance, both commercial APTT-reagents, with or without contact activator, such as kaolin or ellaginic acid, and synthetic phospholipids or phospholipid mixtures have been found usable.

In certain cases, the addition of prothrombin, FX and/or FVIII has been found advantageous. With respect to all coagulation proteins used in accordance with the present method, it will be understood that these coagulation proteins are not limited with respect to species origin and that they are embraced by the invention irrespective of whether they are extracted from plasma or prepared via recombinant techniques from native or molecular biologically modified variants thereof. With regard to species origin, however, mammal origin is normally preferred, and then particularly human, bovine or porcine origin.

The proportions in which the majority of components are present when applying the present method are not particularly critical. However, in order to facilitate an understanding of the invention, suitable concentration ranges for a number of components have been set forth in the following Table A.

TABLE A

| Component/ conditions | Final Content in Test |
| --- | --- |
| Plasma | 0.02-10 percent by volume, particularly 0.1-2 percent by volume* up to 50 percent by volume** |
| $FIX_a$ | $1 \cdot 10^{-15} - 1 \cdot 10^{-6}$ mol/l*** |
| APC | $5 \cdot 10^{-11} - 1 \cdot 10^{-7}$ mol/l, preferably $1 \cdot 10^{-10} - 1 \cdot 10^{-8}$ mol/l |
| $FV_a$ | $1 \cdot 10^{-12} - 1 \cdot 10^{-9}$ mol/l, preferably $2 \cdot 10^{-10} - 1 \cdot 10^{-11}$ mol/l |
| Phospholipids | $1 \cdot 10^{-6} - 3 \cdot 10^{-4}$ mol/l, preferably $3 \cdot 10^{-6} - 1 \cdot 10^{-4}$ mol/l |
| $Ca^{2+}$ | $10^{-4} - 5 \cdot 10^{-2}$ mol/l, preferably $10^{-3} - 10^{-2}$ mol/l**** |

TABLE A-continued

| Component/ conditions | Final Content in Test |
| --- | --- |
| Thrombin substrate, e.g. chromogenic | $2 \cdot 10^{-6} - 2 \cdot 10^{-3}$ mol/l, preferably $10^{-4} - 10^{-3}$ mmol/l |
| pH | 6.5-9.5, preferably 7-8.5 |
| Ion strength (I) | 0-0.6, preferably 0-0.25 |
| Protac ® C | $5 \cdot 10^{-3} - 1.5$ U/ml |
| Prothrombin | $1 \cdot 10^{-9} - 2 \cdot 10^{-6}$ mol/l |
| FX | $1 \cdot 10^{-13} - 5 \cdot 10^{-8}$ mol/l |
| FVIII | $1 \cdot 10^{-4} - 5 \cdot 10^{-1}$ IU/ml |

*Thrombin substrate method, e.g. chromogen method.
**Coagulation method.
***Higher contents in test without an addition of FVIII and/or $FV_a$.
****Calcium may be added in the form of $CaCl_2$ or some other suitable salt.

In order to maintain the pH in the range preferred, the component-solutions are prepared in buffer solutions, using conventional buffer types, such as Tris-buffer.

The inventive method involves incubating the sample at a temperature of 18°-45° C., preferably 35°-40° C. and more preferably at 37° C., for a short period of time, e.g. 0.5-15 minutes, suitably 1-10 minutes and particularly 0.5-6 minutes, whereafter the functional activity of Protein S or C is measured, all in accordance with a so-called single-stage method. In the case of systems having pronounced short reaction times, such as preferably coagulation-based methods, it is preferred to heat the sample in an introductory stage, optionally together with a coagulation factor, to the same temperatures as those recited above, over a short period of time, normally 2-3 minutes, before adding $FIX_a$ and optionally also other coagulation factors to the sample. In certain cases, it may be advantageous to apply a two-stage method incorporating two incubation periods, for instance when Protac ® C is used to activate Protein C in the plasma sample.

It may also be beneficial to use in the present method polyclonal or monoclonal antibodies against a coagulation factor, with the intention of eliminating the influence of this factor. For instance, the biological activity of FVIII can be blocked by adding anti-FVIII:C antibodies.

The aforesaid applies generally for assaying the functional activity of Protein S. When the present method is applied for assaying the functional activity of Protein C, it may be necessary to make some modification. For instance, Protein S, preferably of human origin, is added to the plasma sample either before or after activation of Protein C in the plasma sample, this activation advantageously being effected with Protac ® C, as disclosed above. $FIX_a$ and optionally other coagulation factors is, or are, then added in a second stage.

Figure 1:
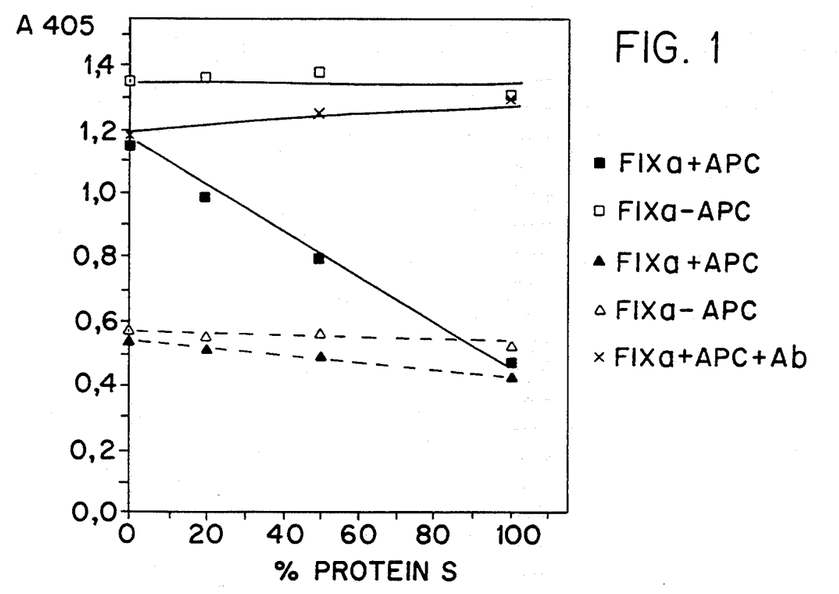
FIG. 1 is a graph which plots Absorbances$_{405}$ against % Protein S for $FIX_3$+APC ( ), $FIX_a$—APC (□), $FX_a$+APC ( ), $FX_a$—APC (Δ), and $FIX_a$/APC+Ab (×) as described in the test for Example 1 below.
Figure 2:
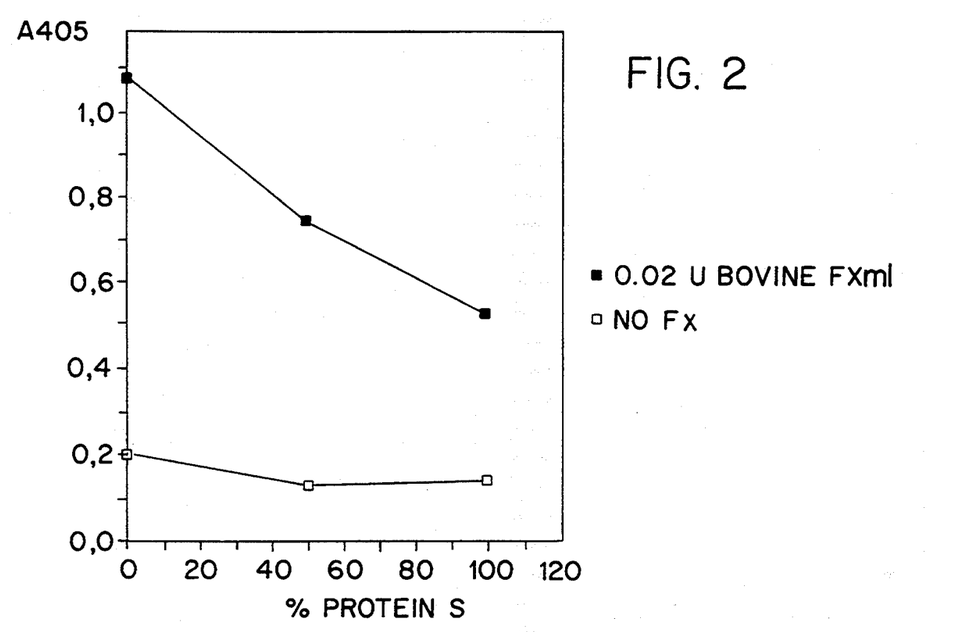
FIG. 2 is a graph which plots Absorbance$_{405}$ against % Protein S for plasma samples containing 0.02U FX/ml ( ), and without addition of non-bovine FX (□), as described in the test of Example 2 below.
Figure 3:
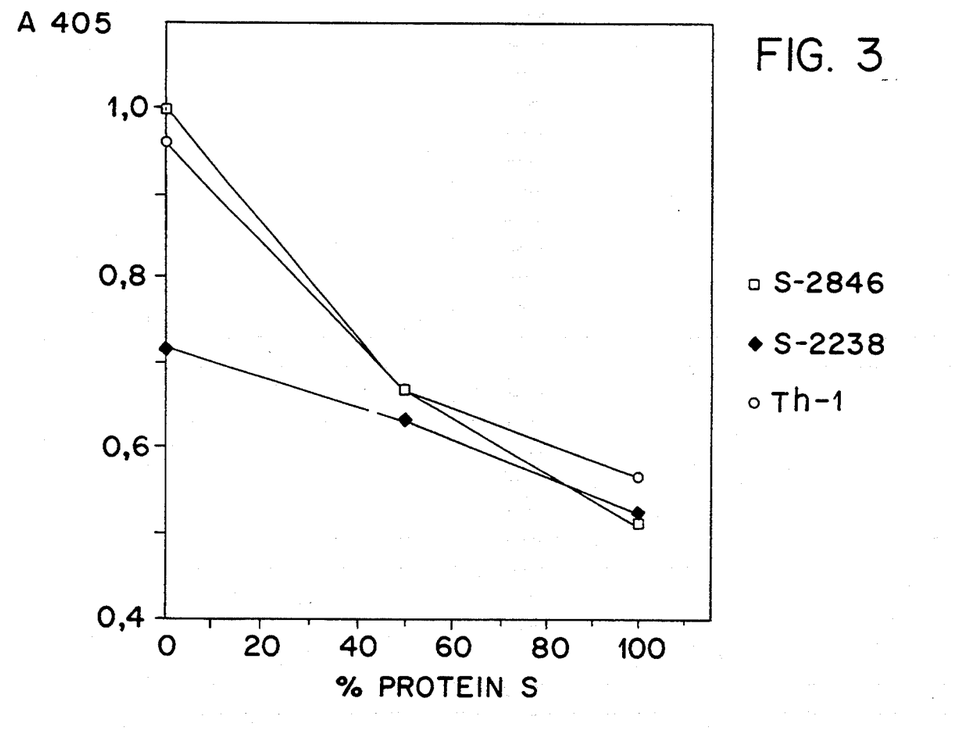
FIG. 3 is a graph which plots Absorbance$_{405}$ against % Protein S for plasma samples incubated with the substrates identified as S-2846 (□), S-2238 ( ), and Th-1 (○), as described in Example 5 below.
Figure 4:
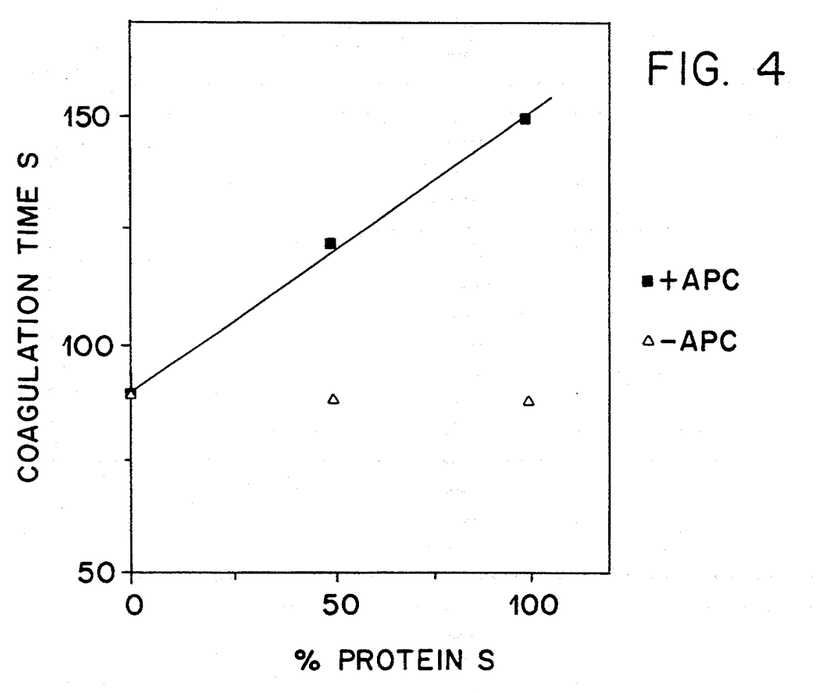
FIG. 4 is a graph which plots the coagulation time, in seconds, against the % Protein S for +APC ( ), and −APC (a) , as described in Example 6 below.
Figure 5:
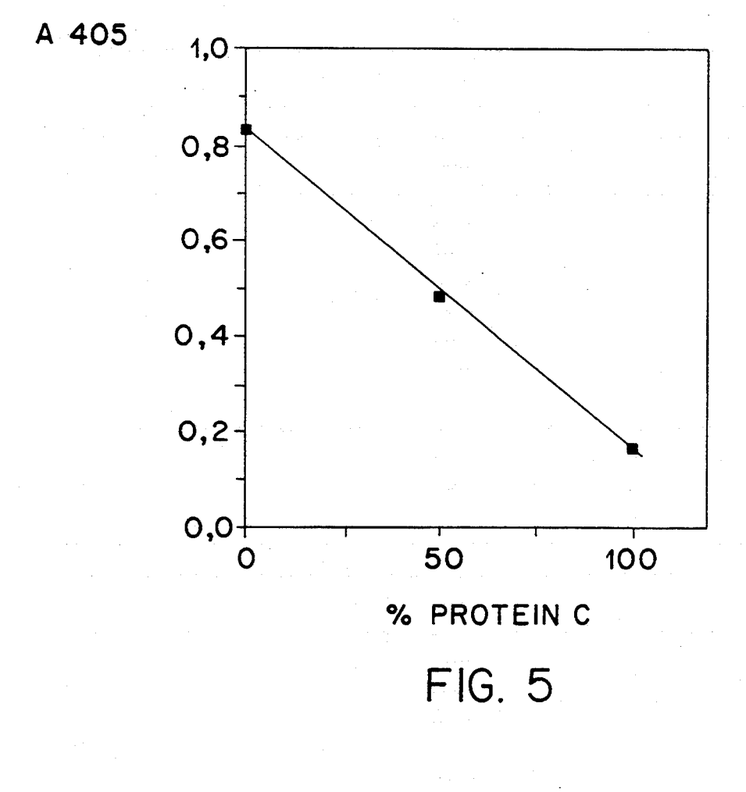
FIG. 5 is a graph which plots Absorbance$_{405}$ against % Protein C as described in the test of Example 7 below.

The invention will be explained in more detail with the aid of the following examples, which are intended solely to illustrate the invention without limiting the scope thereof. These examples include references to the accompanying drawings, of which FIG. 1 illustrates the assaying of Protein S with a chromogenic single-stage method in the presence of FIX$_a$ or FX$_a$; FIG. 2 illustrates the effect of anti-FVIII:C antibodies and bovine FX when assaying Protein S; FIG. 3 illustrates the effect of various substrates in a single-stage method for assaying Protein S; FIG. 4 illustrates a single-stage coagulation-based method for assaying Protein S on the basis of a FIX$_a$ addition; and FIG. 5 illustrates a FIX$_a$-based chromogenic method for assaying Protein C.

Example 1

(a) A plasma sample was diluted 1:15 in Tris-buffer I. 100 μl thereof were mixed with 100 μl of human APC dissolved in Tris-buffer I, 200 μl of a chromogenic substrate H-D-Ala-Pro-Arg-pNA (S2846) from KabiVitrum Diagnostica, Sweden) and 200 μl in total of human FIX$_a$ dissolved in Tris-buffer II, CaCl$_2$, bovine FV$_a$ dissolved in Tris-buffer I and a phospholipid mixture comprising 40% cholesterol, 40% phosphatidylcholine and 20% phosphatidyl serine.

The Tris-buffer I comprised 0.05 mol/l Tris-HCl having a pH of 7.4 and an ion strength (I) of 0.15, and 0.2% bovine serum albumin (BSA).

The Tris-buffer II comprised 0.05 mol/l Tris-HCl, pH 8.0, I=0.15 and 0.2% BSA. The concentrations of the starting solutions were such as to obtain the final concentrations given for the reactants in Table 1.

TABLE 1

| Component | Added Volume | Final Content |
|---|---|---|
| Plasma | 100 μl | 1 percent by volume |
| Human APC | 100 μl | 1 nmol/l |
| H-D-Ala—Pro—Arg-pNA (S-2846) | 200 μl | 0.33 mmol/l |
| FIX$_a$ | | 0.1 nmol/l |
| FV$_a$ | 200 μl | 75 pmol/l |
| CaCl$_2$ | 5 mmol/l | |
| Phosphlipid | | 12 μmol/l |
| | 600 μl | (total volume) |

The mixture was incubated for 4 minutes at 37° C., whereafter 20% -acetic acid was added, with the intention of interrupting the reaction processes. The absorbance of the sample was then determined at 405 nm (A$_{405}$) with standard equipment, such as a photometer, e.g. Hitachi 100-20. A$_{405}$ was also determined for standard samples prepared by mixing normal plasma, the Protein S content of which was set at 100%, and Protein S-deficient plasma, the Protein S content of which was set at 0%. A$_{405}$ was also measured for such plasma as that containing 100% PS and 0% PS respectively.

The values obtained for A$_{405}$ are plotted against % PS in FIG. 1 (- -). It will be seen from these values that very good resolution was achieved, which is reflected in the wide difference between absorbance at 100% and at 0%, this difference being designated ΔA$_{405}$ (0–100%), namely roughly 0.85. It will also be seen from FIG. 1 that the Protein S content is inversely correlated to the quantity of thrombin formed, i.e. that increasing quantities of PS result in a considerable reduction in the formation of thrombin.

(b) In Example 1 (a), the assay was carried out with the addition of APC to the plasma sample. By way of comparison, an analogous assay was carried out without adding APC, wherein a substantially smaller, not significant difference ΔA$_{405}$ (0–100%) was obtained, i.e. the test had a low resolution degree. This is evident from the plotted values (-□-) in FIG. 1. The measured absorbance remained substantially unchanged at a high level when carrying out the assay according to Example 1 (a) subsequent to initial incubation of the sample with antibodies against Protein S (designated PS-Ab), whereby the biological activity of PS, and therewith also of the APC/PS-complex, was eliminated. The values obtained are also plotted (-x-) in FIG. 1.

(c) By way of comparison with known techniques, an assay was also carried out analogously with 1 (a) above, with the addition of human APC and without the addition of human APC, but with the substitution of FIX$_a$ with bovine FX$_a$ (final concentration 0.4 pmol/l and 5-min. incubation). The A$_{405}$-values obtained are also plotted in FIG. 1 (-Δ- and - -respectively). It will be evident herefrom that no significant values of A$_{405}$ (100–0%) were obtained and that the thrombin formation was constantly relatively low.

Although the incubation time was shortened somewhat when the FX$_a$-addition was increased to a final proportion of 40 pmol/l, the resolution was impaired still further. A slightly better result was achieved when the amount of APC addition was increased, although not even a three-fold increase in the APC-addition gave a ΔA$_{405}$ (0–100%)-value higher than 30% of the value obtained in accordance with Example 1 (a).

Example 1 illustrates a-one-stage chromogenic method for assaying the functional activity of PS in plasma. The surprisingly high effect achieved when adding FIX$_a$ to the sample is clearly evident from the results obtained (set forth in FIG. 1). It is admittedly known that APC will degrade the cofactors FV and FVIII via proteolytic cleaving (W. KISIEL, W. CANFIELD, L. ERICSSON, E. DAVIE, Anticoagulant Properties of Bovine Plasma Protein C Following Activation by Thrombin. Biochemistry 16, 5824–5831 (1977); and R. MARLAR, A. KLEISS, J. GRIFFIN, "Mechanism of Action of Human Activated Protein C, a Thrombin-Dependent Anticoagulant Enzyme". Blood 59, 1067–1072 (1982)), which process, however, is not effective before FV and FVIII have been activated respectively to FV$_a$ and FVIII$_a$ by thrombin and-/or FX$_a$. Consequently, it is quite surprising that the addition of a preformed FX$_a$ will result in considerably lower APC/PS activity than the addition of formation of FX$_a$ during incubation, since activation of FVIII via the influence of FX$_a$/thrombin can take place in both instances.

The following Example illustrates the significance of the cofactor FVIII$_a$ to thrombin formation by blocking the activity of the cofactor.

Example 2

One volume of normal plasma (100% PS) was preincubated at 37° C. for 15 minutes with one volume of 0.2 μg/ml of monoclonal anti-FVIII:C antibodies 2A3 (from Kabi AB, Sweden). These antibodies bind specifically to FVIII, which is thereby inactivated. Analogously with Example 1 (a), but with a plasma content of 1.7% and with an $FIX_a$-addition, $A_{405}$ was determined for plasma samples having 0, 50 and 100% PS respectively after incubation for 4 minutes at 37° C., and with an addition (final content 0.02 U/ml) of bovine FX or without such an addition. The values obtained are plotted in FIG. 2. It will be evident herefrom that in the absence of $FVIII_a$, APC/PS will still produce an effect when adding FX (- -), namely through the influence of APC/PS on the $FV_a$ supplied.

In comparison with Example 1 (c), comprising direct addition of $FX_a$ (FIG. 1; - -), it would again appear advantageous to form $FX_a$ during the incubation period, from FX that has been added instead of adding $FX_a$ directly to the system. (FIG. 2; - -).

Example 3

Analogously with Example 1 (a), $A_{405}$ was determined for normal plasma (100% PS) and Protein S deficient plasma (0% PS). Instead of using APC, however, Protac® C (final content 0.17 U/ml) was used, which activates (final content 0.17 U/ml) was used, which activates Protein C to APC upon incubation for 2 minutes at 37° C., and while using 12 pmol/l of $FIX_a$ and applying an incubation time of 4.5 minutes. The results obtained are set forth in Table 2.

TABLE 2

| | $A_{405}$ | |
|---|---|---|
| | + Protac® C | − Protac® C |
| Protein S-deficient plasma (0% PS) | 0.87 | — |
| Normal plasma (100% PS) | 0.18 | 1.6 |

It will seen from these values that Protein S exhibits high activity in the presence of APC. It is not necessary to supply APC initially, since APC can be formed in vitro through the action of Protac® C.

Example 4

$A_{405}$ for normal plasma and Protein S-deficient plasma was assayed analogously with Example 1 (a), although with a final proportion of 18 μmol/l of the synthetic phospholipid mixture. Analogous assays were also made with the aid of an APTT-reagent, Cephotest® (from Nycomed AS, Norway), which also includes a contact activator, namely ellaginic acid, instead of the phospholipid mixture, which in this case comprised an extract from bovine brain. The values obtained are set forth in Table 3.

TABLE 3

COMPARISON BETWEEN CEPHOTEST® AND SYNTHETIC PHOSPHOLIPID (PL) MIXTURE

| | $A_{405}$ | |
|---|---|---|
| % Protein S | Cephotest® | PL-mixture |
| 0 | 0.48 | 0.44 |
| 100 | 0.15 | 0.18 |

These $A_{405}$ values exhibit good agreement, which indicates that different phospholipid sources can be used, including mutually different compositions of synthetic phospholipids and also mutually different contact activators.

Example 5

Analogously with Example 1 (a), plasma containing different percentages of PS were incubated in a single-stage method with the use of three different substrates and additions of bovine $FIX_a$.

The final sample had a plasma content of 1.1 percent by volume, a substrate content of 0.3 mmol/l and contained 0.1 nmol/l $FIX_a$, 75 pmol/l $FV_a$ and 2 nmol/l APC. The substrates tested consisted of S-2846 and S-2238 (both from KabiVitrum Diagnostica, Sweden) and Nycomed Th-1, the incubation times being 4 min., 5 min. and 4 min. respectively.

The results are set forth in FIG. 3. It will be seen from these results that S-2846 (-□-) is a far better substrate than S-2238 (- -). It will also be seen from FIG. 3 that a good effect was also obtained with the substrate Nycomed Th-1, (-○-) (from Nycomd AS, Oslo, Norway).

For comparison purposes, the aforesaid method was also carried out as a two-stage method with the use of substrates S-2846 and S-2238, i.e. the plasma sample to which APC was added was incubated prior to the substrate addition. In the two-stage method, the $\Delta A_{405}$ (0–100%)-values obtained were 0.8 and 0.6 respectively, i.e. no pronounced difference in effectiveness was observed. The following substrates were also tested in a single-stage method and found to be useful, ($\Delta A_{405}$ (0–100%)=0.2–0.5).

Chromozym Th: Tosyl-Gly-Pro-Arg-pNA (from Pentapharm AB, Basel, Switzerland).

Spectrozym Th: H-D-CT-Ala-Arg-pNA (from American Diagnostica, Greenwich, U.S.A. ).

CBS 34.47: H-D-CHG-But-Arg-pNA (from Diagnostica Stago, Asnieres, France).

Thrombin substrate from Behring: H-D-CHA-But-Arg-pNA (from Behringwerke AG, Marburg, Federal Republic of Germany).

wherein
CHT = cyclohexyltyrosine
CHG = cyclohexylglycine
But = α-amino butyric acid
CHA = cyclohexylalanine
pNA = p-nitroanilide
Tosyl = p-toluene sulphonyl

Example 6

100 μl of human APC were added to 100 μl of a plasma sample diluted to 1:1 in a 0.9% -NaCl solution and the sample was incubated for 2 minutes at 37° C. 100 μl totally of bovine $FIX_a$, bovine $FV_a$, Cephotest® and $CaCl_2$ were then added. The contents of the starting solutions used were such as to obtain the following final concentrations:

TABLE 4

| Component | Final Content |
|---|---|
| APC | 15 nmol/l |
| $FIX_a$ | 0.4 nmol/l |
| $FV_a$ | 75 pmol/l |
| Cephotest® | 4.2 percent by volume |
| $Ca^{2+}$ | 4.2 mmol/l |

Plasma samples with 0, 50 and 100% PS, i.e. Protein S-deficient plasma (0%), normal plasma (100%) and a 1:1 mixture (50%) thereof were used in the assay, which was carried out as a single-stage coagulation-based method. The coagulation times of these samples are registered and plotted (FIG. 4; - -) against % PS for the sample.

Analogously with the aforegoing, the coagulation time was also recorded for plasma samples which had not been activated with APC (see FIG. 4; -Δ-).

As will be seen from FIG. 4, an almost 60 second extension of the coagulation time was achieved for 100% PS in comparison with 0% PS, this effect being a considerable improvement on the effect achieved with earlier known methods which lie closest to the afore-described method with respect to plasma content (P. Comp et al, loc cit; B. Dahlbäck, loc cit). No difference (i.e. no extension) in coagulation time between 0 and 100% PS in the above method is obtained in the absence of an APC-addition (-Δ-).

Example 7

A plasma sample to which human Protein S was added was diluted 1:15 with Tris-buffer I. 100 μl of the sample were mixed with 100 μl of Protac® C at a concentration such that the content when activating Protein C was 0.17 U/ml, whereafter the sample was incubated at 37° C. for 5 minutes for activation of PC.

200 μl of thrombin substrate S-2846 were then added together with a total of 200 μl of bovine $FIX_a$ in Tris-buffer II, bovine $FV_a$ in Tris-buffer I, Cephotest® and $CaCl_2$, the concentrations used being such as to obtain the final concentrations given below. The test solution obtained was incubated for 6 minutes at 37° C., whereafter the reaction was interrupted by adding 200 μl of 20% -acetic acid.

This process was carried out with plasma samples having the PC contents and final contents of the included components given below:

0% PC=Protein C-deficient plasma.
50% PC=A mixture of equal parts of normal plasma and Protein C-deficient plasma.
100% PC=Normal plasma.

| Component | Content |
| --- | --- |
| Added human Protein S | 0.11 μg/ml |
| $FIX_a$ | 16 pmol/l |
| $FV_a$ | 75 pmol/l |
| Cephotest® | 4.2 percent by volume |
| $Ca^{2+}$ | 4.2 mmol/l |

$A_{405}$ was measured for these plasma and the values obtained are plotted against the PC contents (%) in FIG. 5. It will be seen that good resolution was obtained, i.e. a high value of $\Delta A_{405}$ (0–100%) of 0.65.

The Figure also shows that the quantity of thrombin formed is clearly and inversely correlated to the proportion of Protein C in plasma. This is also supported by the fact that, as expected, no APC-activity whatsoever was obtained when plasma samples were preincubated with polyclonal anti-PC-antibodies for 5 minutes prior to the activating with Protac® C.

Example 8

The method has been tested clinically, where the method according to Example 1 (a) was carried out with plasma from an individual having normal Protein S content and with plasma from a thrombosis patient. For control purposes, the free Protein S content was also assayed by a conventional RIA-method ("Radio Immuno Assay").

The result achieved when practicing the invention was 115% PS and 53% PS respectively, which is in good agreement with the RIA values of 100% PS and 41% PS respectively.

I claim:

1. A method for determining in a human plasma sample containing 0.02 to 50 percent plasma by volume the functional activity of free Protein S or Protein C, said method comprising:
   (i) adding to said plasma sample a snake venom enzyme which activates protein C or activated Protein C when Protein S is to be determined, or a snake venom enzyme which activates protein C and Protein S when Protein C is to be determined,
   (ii) adding (a) coagulation enzyme $FIX_a$ in an amount of $1 \times 10^{-15}$ to $1 \times 10^{-6}$ mol/l, (b) at least one further coagulation reagent selected from the group consisting of cofactor $FV_a$ in an amount of $1 \times 10^{-12}$ to $1 \times 10^{-9}$ mol/l and phospholipids in an amount of $1 \times 10^{-6}$ to $3 \times 10^{-4}$ mol/l, (c) calcium ions in an amount of $10^{-4}$ to $5 \times 10^{-2}$ mol/l and (d) a buffer to maintain a pH of 6.5 to 9.5 and having an ion strength of 0 to 0.6, to form a mixture and incubating said mixture to form thrombin from prothrombin,
   (iii) measuring the quantity of thrombin formed; and
   (iv) determining the content of functionally active Protein S or functionally active Protein C in the original plasma sample on the basis of the measured quantity of thrombin by comparing the measured quantity with a standard; the content of Protein S or Protein C being inversely related to the quantity of thrombin formed.

2. The method according to claim 1, wherein the mixture after step (i) is incubated at a temperature between 18°–45° C. for 0.5–15 minutes before the addition of $FIX_a$ in step (ii).

3. The method according to claim 1, wherein the measuring of thrombin is carried out by means of substrate cleaving or coagulation.

4. The method according to claim 1, wherein thrombin is measured by use of a chromogenic thrombin substrate, the conversion of which is followed spectrophotometrically.

5. The method according to claim 1, wherein thrombin is measured photometrically by use of a chromogenic thrombin substrate enabling the method to be carried out in one stage.

6. The method according to claim 1, wherein thrombin is measured photometrically by use of a chromogenic thrombin substrate enabling the method to be carried out in one stage, said substrate being selected from the group consisting of H-D-Ala-Pro-Arg-pNA, H-D-CHG-Ala-Arg-pNA, tosyl-Gly-Pro-Arg-pNA, H-D-CHT-Ala-Arg-pNA, and H-D-CHG-But-Arg-pNA.

7. The method according to claim 1, wherein thrombin is measured by means of substrate cleaving, and wherein the final plasma content is 0.02–10 percent by volume.

8. The method according to claim 7, wherein the final plasma content is 0.1–2 percent by volume.

9. The method according to claim 1, wherein $FIX_a$ and cofactor $V_a$ are of mammalian origin.

10. The method according to claim 9, wherein the mammalian origin is selected from bovine, human, and porcine origin.

11. The method according to claim 1, wherein the plasma sample is preincubated with an antibody against FVIII in order to inactivate FVIII.

12. The method of claim 1, wherein the content of plasma in the plasma sample is 0.1 to 2 percent by volume, and the measuring of thrombin is carried out by means of substrate cleaving.

13. The method of claim 12 wherein the amount of $FV_a$ is $2 \times 10^{-10}$ to $1 \times 10^{-11}$ mol/l.

14. The method claim 1, wherein the content of plasma in the plasma sample is from 0.1 to 50%, and the measuring of thrombin is carried out by means of coagulation.

15. The method of claim 14 wherein the amount of $FV_a$ is $2 \times 10^{-10}$ to $1 \times 10^{-11}$ mol/l.

16. The method of claim 1 wherein the amount of $FV_a$ is $2 \times 10^{-10}$ to $1 \times 10^{-11}$ mol/l.

* * * * *